US005843875A

United States Patent [19]
Wei et al.

[11] Patent Number: 5,843,875
[45] Date of Patent: Dec. 1, 1998

[54] PERFUME DELIVERY SYSTEMS IN LIQUID PERSONAL CLEANSING

[75] Inventors: Karl Shiqing Wei; Louis Fay Wong, both of Mason; Mark Richard Sine, Morrow; Timothy Woodrow Coffindaffer, Loveland; Toan Trinh, Maineville, all of Ohio

[73] Assignee: The Procter & Gamble Company, Cincinnati, Ohio

[21] Appl. No.: 667,136

[22] Filed: Jun. 20, 1996

[51] Int. Cl.$^6$ .............................. C11D 3/50; C11D 3/37
[52] U.S. Cl. ................... 510/101; 510/121; 510/127; 510/151; 510/473
[58] Field of Search ............... 510/121, 127, 510/151, 158, 403, 426, 427, 470, 473, 474, 504, 101

[56] References Cited

U.S. PATENT DOCUMENTS

| | | | |
|---|---|---|---|
| 3,580,853 | 5/1971 | Parran, Jr. | 252/152 |
| 4,438,095 | 3/1984 | Grollier et al. | 424/70 |
| 4,673,525 | 6/1987 | Small et al. | 252/132 |
| 4,832,872 | 5/1989 | Scandel | 252/547 |
| 5,037,818 | 8/1991 | Sime | 514/183 |
| 5,085,857 | 2/1992 | Murray | 424/70 |
| 5,093,112 | 3/1992 | Birtwistle et al. | 424/70 |
| 5,186,928 | 2/1993 | Birtwistle | 424/70 |
| 5,211,883 | 5/1993 | Yamashina et al. | 252/546 |
| 5,302,322 | 4/1994 | Birtwistle et al. | 252/547 |
| 5,312,559 | 5/1994 | Kacher et al. | 252/125 |
| 5,352,386 | 10/1994 | Rahman et al. | 252/548 |
| 5,409,628 | 4/1995 | Heinz et al. | 252/174.17 |
| 5,599,483 | 2/1997 | Mizushima et al. | 510/119 |

FOREIGN PATENT DOCUMENTS

| | | | |
|---|---|---|---|
| 0369741 A2 | 5/1990 | European Pat. Off. | A61K 7/06 |
| 0674898 A2 | 4/1995 | European Pat. Off. | A61K 7/075 |
| 2 712 490 | 5/1995 | France | A61K 7/075 |
| 2242899 | 9/1990 | Japan | A61K 7/46 |
| 2177108A | 1/1987 | United Kingdom | C11D 1/65 |
| WO 95/01152 | 1/1995 | WIPO | A61K 7/06 |
| WO 95/22311 | 8/1995 | WIPO | A61K 7/48 |
| 9725975 | 7/1997 | WIPO | A61K 7/50 |

*Primary Examiner*—Douglas J. McGinty
*Assistant Examiner*—John R. Hardee
*Attorney, Agent, or Firm*—Darryl C. Little; Tara M. Rosnell; George W. Allen

[57] ABSTRACT

Disclosed are liquid personal cleansing compositions comprising a specific surfactant component comprising an ethoxylated alkyl sulfate surfactant having from about 1 to about 8 moles of ethoxylation and an amphoteric surfactant, a select soluble cellulosic cationic organic polymer, and a volatile perfume.

8 Claims, No Drawings

PERFUME DELIVERY SYSTEMS IN LIQUID PERSONAL CLEANSING

TECHNICAL FIELD

This invention relates to liquid personal cleansing compositions containing a specific surfactant component comprising an ethoxylated alkyl sulfate surfactant having from about 1 to about 8 moles of ethoxylation and an amphoteric surfactant, a select soluble cellulosic cationic organic polymer, and a volatile perfume. The compositions provide enhanced perfume deposition and provide increased on-skin fragrance delivery.

BACKGROUND OF THE INVENTION

Perfumes and fragrances are typically added to personal cleansing compositions to provide a fresh, clean impression for the compositions. Many consumers would prefer for the perfumes present in the compositions to deposit on their skin to a greater extent and to remain there for an extended period of time to convey a lasting impression of freshness. However, due to the volatility of many perfumes, it can be difficult to deliver this benefit to consumers.

Cationic deposition polymers have been used in the past to enhance deposition of certain nonvolatile components from shampoos and other personal cleansing compositions. For example, U.S. Pat. Nos. 5,037,818 and 5,085,857 describe the use of cationic guar gum to enhance the deposition of antidandruff particles and insoluble nonvolatile silicone, respectively. Deposition polymers have also been proposed to enhance the deposition of sunscreen materials from a shampoo composition. In EP 386,898 a cationic polygalactomannan gum derivative is used. WO 95/22311 describes the use of certain cationic polymers to increase the deposition of nonvolatile benefit agents which include silicones, fats and oils, waxes, hydrocarbons, fatty acids and fatty alcohols, lipids, vitamins and sunscreens.

It would be desirable, however, to increase the deposition of volatile ingredients, such as perfumes, and to provide increased on-skin longevity with respect to these ingredients. This benefit is provided by the present invention.

SUMMARY OF THE INVENTION

The present invention is directed to liquid personal cleansing compositions comprising:
a) from about 5.0% to about 50% of a surfactant component comprising: i) an ethoxylated alkyl sulfate surfactant having from about 1 to about 8 moles of ethoxylation; and ii) an amphoteric surfactant;
b) from about 0.5% to about 5.0% of a cationic cellulosic polymer having a molecular weight of from about 400,000 to about 1,500,000 and charge density of from about 0.6 to about 3 meq/g.;
c) from about 0.01% to about 5% of a volatile perfume; and
d) water.
wherein the ratio of the cationic cellulose polymer to the ethoxylated alkyl sulfate surfactant ranges from about 1:15 to about 1:5; and
wherein said composition comprises less than about 5% of ethoxylated alkyl sulfate surfactant having less than 1 mole of ethoxylation. The personal cleansing compositions provide enhanced perfume deposition and provide increased on-skin fragrance delivery.

DETAILED DESCRIPTION OF THE INVENTION

The present invention is directed to liquid personal cleansing compositions which provide enhanced perfume deposition on the skin and which provide increased on-skin fragrance longevity. The liquid personal cleansing compositions of the present invention comprise a cationic cellulosic polymer, a volatile perfume, a surfactant component comprising an ethoxylated alkyl sulfate surfactant having from about 1 to about 8 moles of ethoxylation, and amphoteric surfactant, and water. The liquid personal cleansing compositions of the present invention have particular ratios of cationic cellulosic polymer to ethoxylated alkyl sulfate surfactant and contain less than 5% of ethoxylated alkyl surfactant having less than 1 mole of ethoxylation.

As used herein, "personal cleansing compositions" refers to any cleansing composition which can be used on the human body. Such compositions would include, for example, shower gel compositions, hand soaps, and shampoos. The liquid personal cleansing compositions of the present invention, including the components comprising them and processes for making them, are described in detail as follows:

I. The Ingredients

A. Surfactant Component

The liquid personal cleansing compositions of the present invention comprise from about 5.0% to about 50%, preferably from about 8% to about 30%, more preferably from about 10% to about 25%, even more preferably from about 12% to about 20%, of a detersive surfactant component comprising: i) an ethoxylated alkyl sulfate surfactant having from about 1 to about 8 moles of ethoxylation; and ii) an amphoteric surfactant. The resulting composition comprises less than about 5%, preferably less than about 3%, and most preferably less than about 2% of alkyl sulfate ethoxylated surfactant having less than 1 mole of ethoxylation.

The detersive surfactant component can optionally comprise additional detersive surfactants. Such surfactants should be physically and chemically compatible with the essential components described herein, or should not otherwise unduly impair product stability, aesthetics or performance.

1. Alkyl Ether Surfactant

The alkyl ether sulfates have the formula: $RO(C_2H_4O)_xSO_3M$, wherein R is alkyl or alkenyl of from about 8 to about 24 carbon atoms, x is 0.5 to 10, and M is a cation such as ammonium, alkanolamines, such as triethanolamine, monovalent metals, such as sodium and potassium, and polyvalent metal cations, such as magnesium, and calcium. The cation M, of the anionic detersive surfactant should be chosen such that the detersive surfactant component is water soluble. Solubility will depend upon the particular anionic detersive surfactants and cations chosen.

Preferably, R has from about 8 to about 18 carbon atoms, more preferably from about 10 to about 16 carbon atoms, most preferably from about 12 to about 14 carbon atoms in both the alkyl and alkyl ether sulfates. The alkyl ether sulfates are typically made as condensation products of ethylene oxide and monohydric alcohols having from about 8 to about 24 carbon atoms. The alcohols can be derived from fats, e.g., coconut oil, palm kernel or tallow, or can be synthetic. Lauryl alcohol and straight chain alcohols derived from coconut oil or palm kernel are preferred herein. Such alcohols are reacted with between about 1 and about 10, and especially about 3, molar proportions of ethylene oxide and the resulting mixture of molecular species having, for example, an average of 3 moles of ethylene oxide per mole of alcohol, is sulfated and neutralized.

Highly preferred alkyl ether sulfates are those comprising a mixture of individual compounds, said mixture having an average alkyl chain length of from about 10 to about 16 carbon atoms and an average degree of ethoxylation of from about 1 to about 4 moles of ethylene oxide.

2. Amphoteric Surfactant

Suitable amphoteric surfactant components for use in the liquid personal cleansing compositions herein include those which are known for use in personal cleansing compositions or other personal care cleansing composition, and which contain a group that is anionic at the pH of the personal cleansing composition. Concentration of such surfactant components in the personal cleansing composition preferably ranges from about 0.5 % to about 20%, preferably from about 1% to about 10%, more preferably from about 2% to about 5% by weight of the composition. Examples of amphoteric surfactants suitable for use in the personal cleansing compositions herein are described in U.S. Pat. Nos. 5,104,646 (Bolich Jr. et al.), U.S. Pat. No. 5,106,609 (Bolich Jr. et al.), which descriptions are incorporated herein by reference. Examples of amphoteric detersive surfactants which can be used in the compositions of the present invention are those which are broadly described as derivatives of aliphatic secondary and tertiary amines in which the aliphatic radical can be straight or branched chain and wherein one of the aliphatic substituents contains from about 8 to about 18 carbon atoms and one contains an anionic water solubilizing group, e.g., carboxy, sulfonate, sulfate, phosphate, or phosphonate. Examples of compounds falling within this definition are sodium 3-dodecyl-aminopropionate, sodium 3-dodecylaminopropane sulfonate, sodium lauryl sarcosinate, N-alkyltaurines such as the one prepared by reacting dodecylamine with sodium isethionate according to the teaching of U.S. Pat. No. 2,658,072, N-higher alkyl aspartic acids such as those produced according to the teaching of U.S. Pat. No. 2,438,091, and the products sold under the trade name "MIRANOL"™ and described in U.S. Pat. No. 2,528,378.

Other amphoterics, sometimes classified as zwitterionics, such as betaines, can also useful in the present invention. Such zwitterionics are considered as amphoterics in the present invention where the zwitterionic has an attached group that is anionic at the pH of the composition. Examples of betaines useful herein include the high alkyl betaines, such as coco dimethyl carboxymethyl betaine, cocoamidopropyl betaine, cocobetaine, lauryl amidopropyl betaine, oleyl betaine, lauryl dimethyl carboxymethyl betaine, lauryl dimethyl alphacarboxyethyl betaine, cetyl dimethyl carboxymethyl betaine, lauryl bis-(2-hydroxyethyl) carboxymethyl betaine, stearyl bis-(2-hydroxypropyl) carboxymethyl betaine, oleyl dimethyl gamma-carboxypropyl betaine, and lauryl bis-(2-hydroxypropyl)alpha-carboxyethyl betaine. The sulfobetaines may be represented by coco dimethyl sulfopropyl betaine, stearyl dimethyl sulfopropyl betaine, lauryl dimethyl sulfoethyl betaine, lauryl bis-(2-hydroxyethyl) sulfopropyl betaine and the like; amidobetaines and amidosulfobetaines, wherein the RCONH(CH$_2$)$_3$ radical is attached to the nitrogen atom of the betaine are also useful in this invention. Most preferred for use herein is cocoamidopropyl betaine.

The personal cleansing compositions of the present invention may further comprise additional detersive surfactants for use in combination with the alkyl ether and amphoteric detersive surfactants described hereinbefore. Suitable optional surfactants include nonionic surfactants, cationic surfactants, additional anionic surfactants and combinations thereof. Any such surfactant known in the art for use in hair or personal care products may be used, provided that the optional additional surfactant is also chemically and physically compatible with the essential components of the personal cleansing composition, or does not otherwise unduly impair product performance, aesthetics or stability. Concentration of the optional additional surfactants in the personal cleansing composition may vary with the cleaning or lather performance desired, the optional surfactant selected, the desired product concentration, the presence of other components in the composition, and other factors well known in the art.

Other suitable anionic detersive surfactants are the reaction products of fatty acids esterified with isethionic acid and neutralized with sodium hydroxide where, for example, the fatty acids are derived from coconut oil or palm kernel oil; sodium or potassium salts of fatty acid amides of methyl tauride in which the fatty acids, for example, are derived from coconut oil or palm kernel oil. Other similar anionic surfactants are described in U.S. Pat. No. 2,486,921; U.S. Pat. No. 2,486,922; and U.S. Pat. No. 2,396,278, which descriptions are incorporated herein by reference.

Other anionic detersive surfactants suitable for use in the personal cleansing compositions are the succinnates, examples of which include disodium N-octadecylsulfosuccinnate; disodium lauryl sulfosuccinate; diammonium lauryl sulfosuccinate; tetrasodium N-(1, 2-dicarboxyethyl)-N-octadecylsulfosuccinnate; diamyl ester of sodium sulfosuccinic acid; dihexyl ester of sodium sulfosuccinic acid; dioctyl esters of sodium sulfosuccinic acid.

Another class of anionic detersive surfactants suitable for use in the personal cleansing compositions are the beta-alkyloxy alkane sulfonates. These compounds have the following formula:

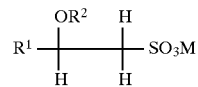

where R$^1$ is a straight chain alkyl group having from about 6 to about 20 carbon atoms, R$^2$ is a lower alkyl group having from about 1 (preferred) to about 3 carbon atoms, and M is a water-soluble cation as hereinbefore described.

Preferred additional anionic detersive surfactants for use in the personal cleansing compositions include ammonium lauryl sulfate, ammonium laureth sulfate, triethylamine lauryl sulfate, triethylamine laureth sulfate, triethanolamine lauryl sulfate, triethanolamine laureth sulfate, monoethanolamine lauryl sulfate, monoethanolamine laureth sulfate, diethanolamine lauryl sulfate, diethanolamine laureth sulfate, lauric monoglyceride sodium sulfate, sodium lauryl sulfate, sodium laureth sulfate, potassium lauryl sulfate, potassium laureth sulfate, sodium lauryl sarcosinate, sodium lauroyl sarcosinate, lauryl sarcosine, cocoyl sarcosine, ammonium cocoyl sulfate, ammonium lauroyl sulfate, sodium cocoyl sulfate, sodium lauroyl sulfate, potassium cocoyl sulfate, potassium lauryl sulfate, triethanolamine lauryl sulfate, triethanolamine lauryl sulfate, monoethanolamine cocoyl sulfate, monoethanolamine lauryl sulfate, sodium tridecyl benzene sulfonate, sodium dodecyl benzene sulfonate, and combinations thereof.

B. Cationic Hair Conditioning Polymer

The liquid personal cleansing compositions of the present invention comprise from about 0.5% to about 5%, preferably from about 0.5% to about 2%, more preferably from about 0.5% to about 1% and most preferably from about 0.6% to about 1% of a cationic cellulose polymer having a molecular weight of from about 400,000 to about 1,500,000 and a charge density of from about 0.6 to about 3 meq/gram. Cationic cellulosic derivative polymer materials suitable for use herein include those of the formula:

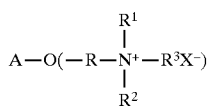

wherein: A is a cellulose anhydroglucose residual,
R is an alkylene, oxyalkylene, polyoxyalkylene, or hydroxyalkylene group, or combination thereof,
$R^1$, $R^2$, and $R^3$ independently are alkyl, aryl, alkylaryl, arylalkyl, alkoxyalkyl, or alkoxyaryl groups, each group containing up to about 18 carbon atoms, and the total number of carbon atoms for each cationic moiety (i.e., the sum of carbon atoms in $R^1$, $R^2$ and $R^3$) preferably being about 20 or less, and
X is an anionic counterion, as previously described.

The cationic cellulosic polymer has a molecular weight ranging from about 400,000 to about 1,500,000, preferably from about 500,000 to about 1,500,000 and most preferably from about 800,000 to about 1,200,000 and a charge density of from about 0.6 to about 3 meq./gr, preferably from about 0.7 to about 2.0 meq/gr. and most preferably from about 0.9 to about 1.5 meq/gr. Cationic cellulose is available from Amerchol Corp. (Edison, N.J., USA) in their Polymer JR and LR series of polymers, as salts of hydroxyethyl cellulose reacted with trimethyl ammonium substituted epoxide, referred to in the industry (CTFA) as Polyquaternium 10.

The water soluble cationic described herein are either soluble in the personal cleansing composition, or preferably are soluble in a complex coacervate phase in the personal cleansing composition formed by the cationic polymer and the anionic surfactant. The complex coacervate is hereinafter described in detail in Section II.

C. THE VOLATILE PERFUME

The liquid personal cleansing compositions of the present invention also contain from about 0.01% to about 5%, preferably from about 0.1% to about 4%, more preferably from about 0.2% to about 2%, and most preferably from about 0.4% to about 2% of a volatile perfume.

The perfume ingredients employed in the personal cleansing compositions of the present invention are the conventional ones known in the art. Selection of the perfume ingredients used in the liquid personal cleansing compositions of the present invention is based solely on the desired fragrance characteristics for the composition.

Suitable perfume compounds and compositions can be found in the art including U.S. Pat. Nos.: 4,145,184, Brain and Cummins, issued Mar. 20, 1979; 4,209,417, Whyte, issued Jun. 24, 1980; 4,515,705, Moeddel, issued May 7, 1985; and 4,152,272, Young, issued May 1, 1979, all of said patents being incorporated herein by reference.

Perfumes can be classified according to their volatility. For purposes of the present invention, "volatile perfumes" are those having a boiling point of less than about 500° C. The highly volatile, low boiling, perfume ingredients typically have boiling points of about 250° C. or lower. The moderately volatile perfume ingredients are those having boiling points of from about 250° C. to about 300° C. The less volatile, high boiling, perfume ingredients are those having boiling points of about 300° C. to about 500° C. Many of the perfume ingredients as discussed hereinafter, along with their odor and/or flavor characters, and their physical and chemical properties, such as boiling point and molecular weight, are given in "Perfume and Flavor Chemicals (Aroma Chemicals)," Steffen Arctander, published by the author, 1969, incorporated herein by reference. It is preferred that the liquid personal cleansing products herein contain at least about 5%, more preferably at least about 25%, and most preferably at least about 50% of highly volatile perfume ingredients having a boiling point of 250° C. or lower.

Examples of the highly volatile, low boiling, perfume ingredients are: anethole, benzaldehyde, benzyl acetate, benzyl alcohol, benzyl formate, iso-bornyl acetate, camphene, cis-citral (neral), citronellal, citronellol, citronellyl acetate, paracymene, decanal, dihydrolinalool, dihydromyrcenol, dimethyl phenyl carbinol, eucalyptol, geranial, geraniol, geranyl acetate, geranyl nitrile, cis-3-hexenyl acetate, hydroxycitronellal, d-limonene, linalool, linalool oxide, linalyl acetate, linalyl propionate, methyl anthranilate, alpha-methyl ionone, methyl nonyl acetaldehyde, methyl phenyl carbinyl acetate, laevo-menthyl acetate, menthone, iso-menthone, myrcene, myrcenyl acetate, myrcenol, nerol, neryl acetate, nonyl acetate, phenyl ethyl alcohol, alpha-pinene, beta-pinene, gamma-terpinene, alpha-terpineol, beta-terpineol, terpinyl acetate, and vertenex (para-tertiary-butyl cyclohexyl acetate). Some natural oils also contain large percentages of highly volatile perfume ingredients. For example, lavandin contains as major components: linalool; linalyl acetate; geraniol; and citronellol. Lemon oil and orange terpenes both contain about 95% of d-limonene.

Examples of moderately volatile perfume ingredients are: amyl cinnamic aldehyde, iso-amyl salicylate, beta-caryophyllene, cedrene, cinnamic alcohol, coumarin, dimethyl benzyl carbinyl acetate, ethyl vanillin, eugenol, iso-eugenol, flor acetate, heliotropine, 3-cis-hexenyl salicylate, hexyl salicylate, lilial (para-tertiarybutyl-alpha-methyl hydrocinnamic aldehyde), gamma-methyl ionone, nerolidol, patchouli alcohol, phenyl hexanol, beta-selinene, trichloromethyl phenyl carbinyl acetate, triethyl citrate, vanillin, and veratraldehyde. Cedarwood terpenes are composed mainly of alpha-cedrene, beta-cedrene, and other $C_{15}H_{24}$ sesquiterpenes.

Examples of the less volatile, high boiling, perfume ingredients are: benzophenone, benzyl salicylate, ethylene brassylate, galaxolide (1,3,4,6,7,8-hexahydro-4,6,6,7,8,8-hexamethyl-cyclopenta-gama-2-benzopyran), hexyl cinnamic aldehyde, lyral (4-(4-hydroxy-4-methyl pentyl)-3-cyclohexene-10-carboxaldehyde), methyl cedrylone, methyl dihydro jasmonate, methyl-beta-naphthyl ketone, musk indanone, musk ketone, musk tibetene, and phenylethyl phenyl acetate.

D. Water

The personal cleansing compositions of the present invention comprise from about 20% to about 95%, preferably from about 40% to about 90%, more preferably from about 60% to about 90%, by weight of water.

E. Other Optional Components

The liquid personal cleansing compositions of this invention do not require the optional ingredients, thus zero is the lowest level for each optional ingredient. Some preferred shower gel compositions contain from about 1% to about 65%, preferably from about 5% to about 50%, more preferably from about 5% to about 20% of selected optional ingredients.

Examples of optional ingredients which can desirably be employed in the liquid personal cleansing compositions of the present invention include, for example, compatible salt and salt hydrates as fillers. Some preferred salts are sodium chloride, sodium sulfate, disodium hydrogen phosphate, sodium pyrophosphate, sodium tetraborate.

Generally, compatible salts and salt hydrates include the sodium, potassium, magnesium, calcium, aluminum, lithium, and ammonium salts of inorganic acids and small (6 carbons or less) carboxylic or other organic acids, corresponding hydrates, and mixtures thereof, are applicable. The inorganic salts include chloride, bromide, sulfate, metasilicate, orthophosphate, pyrophosphate, polyphosphate, metaborate, tetraborate, and carbonate. The organic salts include acetate, formate, methyl sulfate, and citrate.

Water-soluble amine salts can also be used. Monoethanolamine, diethanolamine, and triethanolamine (TEA) chloride salts are preferred.

Aluminosilicates and other clays are also useful in the present invention. Some preferred clays are disclosed in U.S. Pat. Nos. 4,605,509 and 4,274,975, incorporated herein by reference.

Other types of clays include zeolite, kaolinite, montmorillonite, attapulgite, illite, bentonite, and halloysite. Another preferred clay is kaolin.

The liquid personal cleansing compositions of the present invention can contain also other additives commonly included in personal cleansing compositions such as sanitizing or antimicrobial agents, dyes, conditioning/moisturizing agents, preservatives and the like.

Liquid personal cleansing compositions of the present invention can contain silicone gum or fluid, as described in U.S. Pat. Nos.: 4,906,459, Cobb et al., issued Mar. 6, 1990; 4,788,006, Bolich, Jr. et al., issued Nov. 29, 1988; 4,741,855, Grote et al., issued May 3, 1988; 4,728,457, Fieler et al., issued Mar. 1, 1988; 4,704,272, Oh et al., issued Nov. 3, 1987; and 2,826,551, Geen, issued Mar. 11, 1958, all of said patents being incorporated herein by reference.

The silicone component can be present in the liquid personal cleansing compositions of the present invention at a level which is effective to deliver a skin mildness benefit, for example, from about 0.5% to about 20%, preferably from about 1.5% to about 16%, and most preferably from about 3% to about 12% of the composition. Silicone fluid, as used herein, denotes a silicone with viscosities ranging from about 5 to about 600,000 centistokes, most preferably from about 350 to about 100,000 centistokes, at 25° C. Silicone gum, as used herein, denotes a silicone with a mass molecular weight of from about 200,000 to about 1,000,000 and with a viscosity of greater than about 600,000 centistokes. The molecular weight and viscosity of the particular selected siloxanes will determine whether it is a gum or a fluid. The silicone gum and fluid can also be mixed together and incorporated into the compositions of the present invention.

In cases where the liquid personal cleansing composition is prepared via a premix (as hereinafter described in section III), the composition can also optionally contain a neat fragrance.

The levels set out in Other Ingredients Table below are particularly illustrative for liquid shower gel compositions containing other optional ingredients.

OTHER INGREDIENTS TABLE
Practical Wt. % of Other Ingredients

|  | Preferred | More Preferred | Most Preferred |
|---|---|---|---|
| Filler Salts and Salt Hydrates | 0.5–50% | 0.75–25% | 1–15% |
| Water-Soluble Organics | 1.0–50% | 2–40% | 5–20% |
| Polymeric Mildness Enhancers | 0.25%–20% | 0.5%–10% | 1–5% |
| Other Impalpable Water-insolubles | 1–60% | 2–30% | 4–25% |
| Aluminosilicates/Clay | 0.5–25% | 1–10% | 3–8% |

II. The Liquid Personal Cleansing Compositions

The liquid personal cleansing compositions of the present invention have a viscosity ranging from about 100 to about 100,000 centipoise, preferably from about 1,000 to about 50,000 centipoise, most preferably from about 5,000 to about 10,000 centipoise.

The ratio of the cationic cellulosic polymer to ethoxylated alkyl sulfate surfactant in the liquid personal cleansing compositions of the present invention ranges from about 1:100 to about 1:2, preferably from about 1:50 to about 1:5, more preferably from about 1:30 to about 1:5 even more preferably from about 1:20 to about 1:5, and most preferably from about 1:15 to about 1:5.

Without being bound by theory, it is believed that the cationic material and the anionic surfactant present in the personal cleansing compositions herein form coacervates or ion-pairs and that the perfume becomes physically entrapped within the coacervate or ion-pair. The coacervate is believed to deposit onto the skin during the wash/rinse process, thus significantly enhancing deposition of the perfume entrapped therein. It is further believed that the slow release of perfume from the coacervate provides a fragrance longevity benefit.

If the ratio of cationic material:anionic surfactant is less than about 1:100 or greater than about 1:2, the formation of the coacervate is believed to be impeded and the benefit of the invention (e.g., enhanced deposition of perfume and increased longevity of fragrance) is reduced or eliminated, and/or the product is rendered physically unstable.

In addition to the ratio of the cationic cellosic polymer to the ethoxylated alkyl surfactant, coacervate formation is also dependent upon a variety of other criteria such as molecular weight, component concentration, ionic strength (including modification of ionic strength, for example, by addition of salts), charge density of the cationic and anionic components, pH, and temperature. Coacervate systems and the effect of these parameters have been described, for example, by J. Caelles, et al., "Anionic and Cationic Compounds in Mixed Systems", *Cosmetics & Toiletries,* Vol. 106, Apr. 1991, pp 49–54, C. J. van Oss, "Coacervation, Complex-Coacervation and Flocculation", *J Dispersion Science and Technology,* Vol. 9 (5,6), 1988–89, pp 561–573, and D. J. Burgess, "Practical Analysis of Complex Coacervate Systems", *J of Colloid and Interface Science,* Vol. 140, No. 1, November 1990, pp 227–238, which descriptions are incorporated herein by reference.

Techniques for analysis of formation of complex coacervates are known in the art. For example, microscopic analyses of the personal cleansing compositions, at any chosen stage of dilution, can be utilized to identify whether a coacervate phase has formed. Such coacervate phase will be identifiable as an additional emulsified phase in the composition. The use of dyes can aid in distinguishing the coacervate phase from other insoluble phases dispersed in the personal cleansing composition.

The liquid personal cleansing compositions of the present invention provide enhanced deposition of the fragrance on the skin and provide increased on-skin fragrance longevity.

III. Process for Making the Liquid Personal Cleansing Compositions of the Present Invention The liquid personal cleansing compositions of the present invention can be prepared by conventional processes for preparing liquid personal cleansing compositions. In a preferred embodiment for preparing the liquid personal cleansing compositions of the present invention, a premix comprising the cationic cellulosic polymer and the volatile perfume is formed and then added to a base personal cleansing composition which contains the ethoxylated alkyl sulfate surfactant.

When a premix is used to prepare the liquid personal cleansing compositions of the present invention, the liquid personal cleansing composition generally comprises from about 1% to about 50%, preferably from about 5% to about 50%, more preferably from about 10% to about 50% of the premix and from about 50% to about 99%, preferably from about 50% to about 95%, more preferably from about 50% to about 90% of a base personal cleansing composition.

The premix typically comprises from about 0.1% to about 10%, preferably from about 1% to about 10%, more preferably from about 1% to about 5% of the cationic cellulosic polymer, from about 0.1% to about 10%, preferably from about 1% to about 10%, more preferably from about 1% to about 5% of a volatile perfume, and from about 80% to about 99%, preferably from about 90% to about 99%, more preferably from about 95% to about 99% water. The base personal cleansing composition typically comprises from about 1% to about 80%, preferably from about 2% to about 50%, more preferably from about 5% to about 30% total anionic surfactant and from about 20% to about 95%, preferably from about 40% to about 90%, more preferably from about 60% to about 90% water. If optional ingredients are part of the formulation, these are generally included within the base personal cleansing composition.

ANALYTICAL METHODS

1. GC/MS Method for Measuring Perfume Deposition
   1. The skin background is extracted using 5×5 cc acetone for about 30 seconds on the forearm (area about 20 $cm^2$).
   2. One forearm is washed with test product and the other forearm is washed with a control product using a standard arm washing protocol (below).
   3. The total perfume deposited on each arm is extracted using 5×5 cc acetone for about 30 seconds (area of about 20 $cc^2$).
   4. The extracted acetone solution from step 3 is preconcentrated to about 0.5 ml by turbovap.
   5. The perfume components are analyzed and quantitated by GC/MS.

Standard Arm Washing Protocol
   1. Run laboratory tap water at low/moderate flow at about 90°–100° F. Leave water running throughout the entire washing procedure.
   2. Wet the volar portion on the forearm for about 10 seconds.
   3. Apply about 1 cc product to the forearm.
   4. Rub the product from the wrist to the elbow for about 10 seconds to create a lather.
   5. Allow the lather to remain on the skin for about 90 seconds.
   6. Rinse forearm for about 15 seconds with running water, allowing the water stream to hit the lather line on the skin and run down the forearm.
   7. Pat the forearm dry with paper towels.

2. Wash Cloth Method for Measuring Perfume Intensity
   1. Standard white washcloths are cut into approximately 3"×3" swatches.
   2. The swatch is placed under running tap water (about 95°–100° F.) for 5 seconds.
   3. About one (1) cc of test product is placed onto wash cloth.
   4. The cloth is rubbed in between hands for about 15 seconds to generate lather.
   5. The lather is allowed to remain on the cloth for about 30 seconds.
   6. The cloth is rinsed by holding the cloth in the corner and placing it under running tap water (about 95°–100° F.) for about 15 seconds.
   7. The cloth is held in the corner and allowed to drip dry for about 5 seconds.
   8. The cloth is placed between 2 Bounty paper towels folded in half and patted for about 5 seconds.
   9. The dry portion of each Bounty towel is then folded over again and patted for about another 5 seconds.
   10. Steps 1–9 are repeated for control product.
   11. Each cloth (the one with the test product and the one with the control product) is placed on top of a 4 oz. glass jar and allowed to dry overnight. (Do not place lid on jar.)
   11. Each dried cloth is placed inside a glass jar. (Do not put lid on jar).
   12. Ten panelists evaluate the odor intensity of the cloth inside each jar according to the following scale:
   Scale is from 0 to 100:
   0=no perfume odor
   25=slight perfume odor
   50=moderate perfume odor
   100=strong perfume odor
   The panelists can assign any number between 0 and 100. The numbers 0, 25, 50 and 100 are only intended as guidelines and are not to be viewed as the only numbers that can be assigned.
   13. The panelists also indicate any perceived difference in the intensity of the two wash clothes by using a 0 to 4 difference scale:
   0=equal/no difference
   1=I think they are different
   2=I know they are different
   3=There is a lot of difference
   4=a whole lot different
   The panelists may go back and forth between the two samples as much as they need to form an opinion.

3. Arm Wash Method for Measuring Intensity of Perfume
   1. The standard arm wash procedure set forth in Analytical Method 1 is followed.
   2. Panelists are asked to evaluate odor of a test product and a control product at intervals of 0 minutes, about 30 minutes, about 60 minutes and about 120 minutes according to the following scale:
   0=no perfume odor
   25=slight perfume odor
   50=moderate perfume odor
   100=strong perfume odor
   The panelists can assign any number between 0 and 100. The numbers 0, 25, 50 and 100 are only intended as guidelines and are not to be viewed as the only numbers that can be assigned.

EXAMPLES

The following non-limiting examples illustrate the composition of the present invention.

Example 1

Liquid shower gel compositions are prepared as follows:
Shower Gel Test Product
About fifteen (15) grams JR-30M polymer is added to about 750 grams distilled water at room temperature. The solution is stirred overnight until JR-30M polymer is fully hydrated and solution becomes clear.

About five (5) grams of volatile perfume A is mixed in about five (5) grams phenyltrimethicone. Then (10) grams perfume-silicone mixture is added in about eighty (80) grams of the hydrated JR-30M solution to form a premix. The composition of the premix is listed in Table 1.

TABLE 1

Composition of Premix

| | |
|---|---|
| Perfume A | 5.55% |
| Phenytrimethicone | 5.56% |
| Polymer JR-30M | 1.74% |
| Water | 87.15% |
| Total | 100.00% |

The Shower Gel Test Product is made by mixing about 30 grams of the premix from Table 1 into about 70 grams of a shower gel base.

Shower Gel Control Product

A Shower Gel Control Product is made by mixing about 28.3 grams distilled water into about 70 grams of the shower gel base and then adding about 1.67 grams of volatile perfume A. The composition of the Shower Gel Control Product and the Shower Gel Test product are listed in Table 2.

TABLE 2

Compositions of Shower Gels

| Ingredient | Shower Gel Control Product | Shower Gel Test Product |
|---|---|---|
| Na Alkyl Glycerol Ether Sulfonate | 4.28 | 4.28 |
| Coco Betaine | 2.24 | 2.24 |
| Polymer JR-30M (NOT premixed with perfume) | 0.21 | 0.21 |
| Polymer JR-30M (premixed with perfume) | — | 0.60 |
| Phenyltrimethicone | — | 1.67 |
| Perfume A | 1.67 | 1.67 |
| Water and optional ingredients | qs | qs |
| Total | 100.00 | 100.00 |

The total perfume deposition on the skin for the Shower Gel Control Product 10 and for the Shower Gel Test Product is measured according to the GC/MS Method hereinbefore described in the Analytical Methods section. The total perfume deposition on-skin for the Shower Gel Control Product and the Shower Gel Test Product is set forth in Table 3.

TABLE 3

Total Perfume Deposition on-Skin

| Shower Gel Control Product | Shower Gel Test Product |
|---|---|
| 15.1 ng | 84.2 ng |

The perfume deposition of the Shower Gel Test Product is five times higher than the deposition of the Shower Gel Control Product.

The perfume intensity of the Shower Gel Test Product and the Shower Gel Control Product is also analyzed according to the Arm Wash Method and the Wash Cloth Method, both hereinbefore described in the Analytical Methods section.

The intensity of the perfume for each shower gel according to the Arm Wash Method is set forth in Table 4, and the intensity of the perfume for each shower gel according to the Wash Cloth Method is set forth in Table 5.

TABLE 4

Arm Wash Method Perfume Intensity

| | Shower Gel Control Product | Shower Gel Test Product |
|---|---|---|
| Initial | 49 | 78 |
| 30 mins | 29 | 66 |
| 60 mins | 20 | 60 |
| 120 mins | 13 | 45 |

The intensity of the perfume in the Shower Gel Test Product is about 59% higher than the Shower Gel Control Product initially, about 128% higher than the Shower Gel Control Product after about 30 minutes, about 200% higher than the Shower Gel Control Product after about 60 minutes, and about 246% higher than the Shower Gel Control Product after about 120 minutes according to the Arm Wash Method.

TABLE 5

Wash Cloth Method Perfume Intensity (Initial)

| Shower Gel Control Product | Shower Gel Test Product |
|---|---|
| 26 | 48 |

The intensity of the perfume in the Shower Gel Test Product is about 85% higher than the intensity of the perfume in the Shower Gel Control Product according to the Wash Cloth Method.

Example 2

Liquid shower gel composition is prepared as follows:

Shower Gel Test Product A:

About ten (10) grams JR-30M polymer is added to about 490 grams distilled water at room temperature. The solution is stirred overnight until JR-30M polymer is fully hydrated and solution becomes clear.

About 0.20 grams of volatile Perfume B is added to about 15 grams of the hydrated JR-30M polymer solution to form a premix. The composition of the premix is set forth in Table 6.

TABLE 6

Composition of premix

| Ingredient | Premix |
|---|---|
| Perfume B | 1.32% |
| Polymer JR-30M | 1.97% |
| Water | 96.71% |
| Total | 100.00% |

About 15.20 grams of the premix is then mixed with about 34.80 grams of a shower gel base composition to form Shower Gel Test Product A. The composition of Shower Gel Test Product A is set forth in Table 7.

Shower Gel Test Product B

Shower Gel Test Product B is prepared by mixing about 15 grams hydrated JR-30M polymer into about 34.80 grams of the same shower gel base composition used for Shower Gel Test Product A, and then adding about 0.20 grams of volatile Perfume B. The composition of Shower Gel Test Product B is also set forth in Table 7.

Shower Gel Control Product

Shower Gel Control Product is prepared by mixing about 15 grams distilled water into about 34.80 grams of the same shower gel base composition used for Shower Gel Test Product A and B, and then adding about 0.20 grams of volatile Perfume B. The composition of Shower Gel Control Product is also set forth in Table 7.

TABLE 7

Compositions of Shower Gels

| Ingredient | Shower Gel Control | Shower Gel Test Product A | Shower Gel Test Product B |
|---|---|---|---|
| Sodium Laureth Sulfate | 5.80 | 5.80 | 5.80 |
| Cocamidopropyl Betaine | 5.15 | 5.15 | 5.15 |
| Sodium Lauroyl Sarcosinate | 0.50 | 0.50 | 0.50 |
| Perfume B | 0.40 | 0.40 | 0.40 |
| Polymer JR-30M (NOT Premixed with Perfume) | — | — | 0.60 |
| Polymer JR-30M (premixed with perfume) | — | 0.60 | — |
| Water and optional ingredients | qs | qs | qs |
| Total | 100.00 | 100.00 | 100.00 |

The intensity of the perfume in Shower Gel Test Products and B and Shower Gel Control Product, measured according to the Wash Cloth Method is set forth in Table 8.

TABLE 8

Wash Cloth Method Perfume Intensity

| Control Shower Gel Product | Shower Gel Test Product A | Shower Gel Test Product B |
|---|---|---|
| 5 | 43.5 | 13.5 |

The intensity of the perfume in Shower Gel Test Product A is about 770% higher than the intensity of the perfume in the Shower Gel Control Product according to the Wash Cloth Method. The intensity of the perfume in Shower Gel Test Product B is about 220% higher than the intensity of the perfume in the Shower Gel Control Product according to the Wash Cloth Method.

Example 3

Liquid Shower Gel Compositions are prepared as follows:

Shower Gel Test Products A and B

To prepare Shower Gel Test Product A, about 2.00 grams of JR-30M polymer is added to about 98.00 grams water at room temperature. The solution is stirred overnight until the JR-30M polymer is fully hydrated and the solution becomes clear. Then about 0.50 grams of Volatile Perfume C is added into about 15 grams of the hydrated JR-30M solution to form a premix. The composition of the premix for Shower Gel Test Product A is set forth in Table 9.

To prepare Shower Gel Test Product B, 5.00 grams of JR-30M polymer is added to about 95 grams water at room temperature. The solution is stirred overnight until the JR-30M polymer is fully hydrated and the solution becomes clear. Then about 0.50 grams of Volatile Perfume C is added into about 8 grams of the hydrated JR-30M solution to form a premix. The composition of the premix for Shower Gel Test Product B is set forth in Table 9.

TABLE 9

Compositions of premix

| Ingredient | Shower Gel Test Product A Premix | Shower Gel Test Product B Premix |
|---|---|---|
| Perfume C | 3.23% | 5.88 |
| Polymer JR-30M | 1.94% | 4.71 |
| Water | 94.83% | 89.41 |
| Total | 100.00% | 100.00 |

Shower Gel Test Product A is made by mixing about 15.50 grams of the Shower Gel Test Product A Premix into about 34.50 grams of a shower gel base. Shower Gel Test Product B is made by mixing about 8.50 grams of Shower Gel Test Product B Premix into about 41.50 grams of the same shower gel base. The compositions of Shower Gel Test Products A and B are set out in Table 10.

Shower Gel Control Product

The Shower Gel Control Product is prepared by mixing about 15 grams of distilled water into the same shower gel base composition used for Shower Gel Test Products A and B, and then adding about 0.50 grams of volatile Perfume C. The composition of Shower Gel Control Product is set forth in Table 10.

TABLE 10

Compositions of Shower Gels

| Ingredient | Shower Gel Control Product | Shower Gel Test Product A | Shower Gel Test Product B |
|---|---|---|---|
| Sodium Laureth Sulfate | 5.80 | 5.80 | 5.80 |
| Cocamidopropyl Betaine | 5.15 | 5.15 | 5.15 |
| Sodium Lauryl Sarcosinate | 0.50 | 0.50 | 0.50 |
| Perfume C | 1.00 | 1.00 | 1.00 |
| Polymer JR-30M (premixed with perfume) | — | 0.60 | 0.80 |
| Water and optional ingredients | qs | qs | qs |
| Total | 100.00 | 100.00 | 100.00 |

The intensity of the perfume for the Shower Gel Control Product and for Shower Gel Test Products A and B, as measured by the Wash Cloth Method hereinbefore described in the Analytical Methods section, are set forth in Table 11.

TABLE 11

Wash Cloth Method Perfume Intensity (Initial)

| Shower Gel Control Product | Shower Gel Test Product A | Shower Gel Test Product B |
|---|---|---|
| 16 | 37 | 26 |

The intensity of the perfume in Shower Gel Test Product A is about 131% higher than the intensity of the perfume in the Shower Gel Control Product. The intensity of the perfume in Shower Gel Test Product B is about 63% higher than the Shower Gel Control Product.

What is claimed is:

1. A liquid personal cleansing composition comprising:
   a) a premix comprising:
      i) from about 0.5% to about 5% of polyquaternium-10 having a molecular weight of from about 400,000 to about 1,500,000 and charge density of from about 0.6 to about 3 meq/gram; and
  ii) from about 0.01% to about 5% of a volatile perfume;
b) from about 5% to about 50% of a surfactant component comprising:
  i) an ethoxylated alkyl sulfate surfactant having from about 1 to about 8 moles of ethoxylation; and
  ii) cocoamidopropyl betaine; and
c) water;
wherein the ratio of the cationic cellulosic polymer to the ethoxylated alkyl sulfate surfactant ranges from about 1:15 to about 1:5 and wherein said composition comprises less than about 5% of ethoxylated alkyl sulfate surfactant having less than 1 mole of ethoxylation.

2. A liquid personal cleansing composition according to claim 1 which comprises from about 8% to about 30% of said surfactant component and wherein said composition comprises less than about 3% of ethoxylated surfactant having less than 1 mole of ethoxylation and wherein said amphoteric surfactant is cocoamidopropyl betaine.

3. A liquid personal cleansing composition according to claim 2 wherein said cationic cellulosic polymer has a cationic charge density of from about 0.7 meq/gram to about 2.0 meq/gram.

4. A liquid personal cleansing composition according to claim 3 wherein said composition comprises an additional anionic surfactant and wherein said composition comprises less than about 2% of ethoxylated surfactant having less than 1 mole of ethoxylation.

5. A liquid personal cleansing composition according to claim 3 wherein said cationic cellulosic polymer has a cationic charge density of from about 0.9 meq/gram to about 1.5 meq/gram.

6. A liquid personal cleansing composition according to claim 1 wherein said cocoamidopropyl betaine comprises from about 2% to about 6% of the composition.

7. A liquid personal cleansing composition according to claim 6 which contains from about 0.1% to about 4% of the volatile perfume.

8. A liquid personal cleansing composition according to claim 7 wherein the viscosity of the composition ranges from about 100 to about 100,000 centipoise. claim 6 was made dependent from claim 3.

* * * * *

UNITED STATES PATENT AND TRADEMARK OFFICE
CERTIFICATE OF CORRECTION

PATENT NO. : 5,843,875
DATED : December 1, 1998
INVENTOR(S) : Karl S. Wei et al.

It is certified that error appears in the above-identified patent and that said Letters Patent is hereby corrected as shown below:

Column 16,
Line 19, delete "claim 6 was".
Line 20, delete "made dependent from claim 3.".

Signed and Sealed this

Third Day of June, 2003

JAMES E. ROGAN
*Director of the United States Patent and Trademark Office*